United States Patent [19]

Coulson

[11] Patent Number: 5,019,517

[45] Date of Patent: May 28, 1991

[54] SYSTEM, DETECTOR AND METHOD FOR TRACE GASES

[76] Inventor: Dale M. Coulson, 21 Willow Rd., Apt. 13, Menlo Park, Calif. 94025

[21] Appl. No.: 182,153

[22] Filed: Apr. 15, 1988

[51] Int. Cl.$^5$ ............... G01N 21/71; G01N 31/12; G01N 27/62; G01N 25/18

[52] U.S. Cl. ............... 436/753; 436/155; 436/161; 436/149; 422/78; 422/89; 422/98; 73/23.2; 73/23.35; 324/464; 324/468; 324/451

[58] Field of Search ............... 436/153, 154, 124, 155, 436/161, 806, 157, 149, 158; 422/54, 78, 80, 88, 89, 90; 324/451, 464, 468; 73/23.02, 23.35, 25.01, 25.03, 25.05; 338/34

[56] References Cited

U.S. PATENT DOCUMENTS

| | | | |
|---|---|---|---|
| 1,421,720 | 7/1922 | Roberts | 324/464 |
| 1,697,339 | 1/1929 | Baker | 141/8 |
| 1,809,115 | 6/1931 | Goddard | 313/230 |
| 1,914,883 | 6/1933 | Cottrell | 315/108 |
| 2,232,030 | 2/1941 | Kallmann | 313/359.1 |
| 2,334,356 | 11/1943 | Salzberg et al. | 324/462 |
| 2,486,199 | 10/1949 | Nier | 73/40.7 |
| 2,507,321 | 5/1950 | Sherwood | 73/40.7 |
| 2,550,498 | 4/1951 | Rice | 324/468 |
| 2,573,005 | 10/1951 | Glyptis | 324/462 |
| 2,579,352 | 12/1951 | White | 324/468 |
| 2,591,485 | 4/1952 | White | 324/468 |
| 2,706,398 | 4/1955 | Davidson | 73/40.7 |
| 2,795,716 | 6/1957 | Roberts | 313/7 |
| 2,806,181 | 9/1957 | Rockafellow | 315/166 |
| 2,814,018 | 11/1957 | Zemany | 324/468 |
| 2,844,781 | 7/1958 | Adelman et al. | 318/455 |
| 2,873,425 | 2/1959 | Huggins | 324/517 |
| 2,897,437 | 7/1959 | Briggs et al. | 324/468 |
| 2,928,042 | 3/1960 | Lawrance et al. | 324/468 |
| 2,996,661 | 8/1961 | Roberts | 324/468 |
| 3,009,074 | 11/1961 | Roberts | 313/7 |
| 3,065,411 | 11/1962 | Roberts | 324/468 |
| 3,071,722 | 1/1963 | Roberts | 324/468 |
| 3,144,600 | 8/1964 | Roberts | 324/468 |
| 3,372,994 | 3/1968 | Giuffrida | 422/54 |
| 4,203,726 | 5/1980 | Patterson | 436/103 |
| 4,524,047 | 6/1985 | Patterson | 422/98 |

OTHER PUBLICATIONS

Roberts, J. A., "Precision Leaks for Standardizing Leak Detection Equipment"; Committee on Vacuum Techniques, 1956 Vacuum Symposium Transactions (New York Pergamon Press) pp. 124–126.

General Electric H-7 Audible Alarm Leak Detector Product Information (1962).

Giuffrida, Laura and Ives, Fred, "Investigation of Two Gas Chromatographic Techniques for the Determination of Organophospate Pesticide Residues", *Journal of the A.O.A.C.* (vol. 4, No. 6, 1964).

Giuffrida, L. & Ives, N. F. et al, "Gas Chromatography of Pesticides—Improvements in the Use of Special Ionization Detection Systems", *Journal of the A.O.A.C.* (vol. 49, No. 1, 1966), pp. 8–21.

Folmer, O. F., Jr. & Yang, Kang et al, "Use of Catalytic Combustion Filaments for Qualitative Gas Chromatography", *Analytical Chemistry*, vol. 35, No. 4, Apr. 1963, pp. 454–459.

(List continued on next page.)

*Primary Examiner*—Robert J. Warden
*Assistant Examiner*—Theresa A. Trembley
*Attorney, Agent, or Firm*—Flehr, Hohbach, Test, Albritton & Herbert

[57] ABSTRACT

A detector system (10) especially suited for detecting a halogen containing component in a gas stream includes a gas chromatograph (12), which is connected by gas line (13) to pyrolysis chamber (14). Sources (16) of additional gas streams are connected by a gas line (18) to the pyrolysis chamber (14). The detector electrodes in the pyrolysis chamber (14) are electrically connected to detector electronics (20) by line (22). A temperature control circuit (24) is electrically connected to heater (26) by line (28). Heater (26) is thermally coupled to the pyrolysis chamber (b 14) at (30). The pyrolysis chamber (14) is thermally coupled to thermocouple (32) at (34). The thermocouple (32) is electrically connected to the temperature control circuit (24) by line (36). The heater (26) is independent of the detector electrodes and maintains a temperature between about 700 degrees and 1000 degrees Centigrade. The detector electrodes are substantially alkali metal free.

23 Claims, 3 Drawing Sheets

OTHER PUBLICATIONS

Karmen, Arthur & Giuffrida, Laura, "Enhancement of the Response of the Hydrogen Flame Ionization Detector to Compounds Containing Halogens and Phosphorus", *Nature*, Mar. 21, 1964, pp. 120401205.

Lovelock, J. E. & Shoemake, G. R., et al, "Improved Ionization Cross-Section Detectors", *Analytical Chemistry*, vol. 36, No. 8, Jul. 1964, pp. 1410–1415.

Karmen, Arthur, "Specific Detection of Halogens and Phosphorus by Flame Ionization", *Analytical Chemistry*, vol. 36, No. 8, Jul. 1964, pp. 1416–1421.

Ives, N. F. & Giuffrida, Laura, "Investigation of Thermionic Detector Response for the Gas Chromatography of P, N, As, and CI Organic Compounds", *Journal of the A.O.A.C.* (vol. 50, No. 1, 1967), pp. 1–4.

Persky, Avigdor, et al, "Formation of Positive and Negative Ions on Rhenium, Oxygenated Tungsten, Hafnium, Lanthanum Hexaboride, and Thoriated Tungsten Surfaces", *The Journal of Chemical Physics*, vol. 49, No. 1, Sep. 1, 1968, pp. 2347–2357.

Karmen, Arthur, "Differential Specificity in Detecting Phosphorous, Nitrogen, and Halogens with Alkali Flames", *Journal of Chromatographic Science*, Sep. 1969, vol. 7, pp. 541–549.

Hartmann, C. Harold, "Alkali Flame Detector for Organic Nitrogen Compounds", *Journal of Chromatographic Science*, Mar. 1969, vol. 7, pp. 163–167.

Kolb, B. and Bischoff, J., "A New Design of a Thermionic Nitrogen and Phosphorus Detector for GC", *Journal of Chromatographic Science*, Nov. 1974, vol. 12, pp. 625–629.

Kolb, B, and Auer, M. et al, "Reaction Mechanism in an Ionization Detector with Tunable Selectivity for Carbon, Nitrogen and Phosphorus", *Journal of Chromatographic Science*, Feb. 1977, vol. 15, pp. 53–63.

Burgett, Charles A., Smith, Douglas et al, "The Nitrogen–Phosphorus Detector and Its Applications in Gas Chromatography", *Journal of Chromatography*, 134 (1977), pp. 57–70.

Greenhalgh, Roy, "A Pure Rubidium/Quartz Source for Alkali Flame Ionization Detectors", *Journal of Chromatographic Science*, Jan. 1978, vol. 16, pp. 8–11.

Patterson, Paul L. & Howe, Robert L., "Thermionic Nitrogen–Phosphorus Detection with an Alkali–Ceramic Bead", *Journal of Chromatographic Science*, Jul. 1978, vol. 16, pp. 275–280.

Patterson, Paul L., "Selective Responses of a Flameless Thermionic Detector", *Journal of Chromatography*, 167 (1978), pp. 381–397.

Du Puis, M. D., & Hill, H. H., Jr., "Analysis of Gasoline for Antiknock Agents with a Hydrogen Atmosphere Flame Ionization Detector", *Analytical Chemistry*, vol. 51, No. 2, Feb. 1979, pp. 292–295.

Allison, J. & Ridge, D. P., "Reactions of Atomic Metal Ions with Alkyl Halides and Alcohols in the Gas Phase", *Journal of the American Chemical Society*, 101:17, Aug. 15, 1979, pp. 4998–5008.

Olan, K., Szoke, A. & Vajta, Zs., "On the Mechanism of Kolb's N-P Selective Detector", *Journal of Chromatographic Science*, vol. 17, Sep. 1979, pp. 497–502.

Patterson, P. L., Gatten, R. A. et al, "An Improved Thermionic Ionization Detector for Gas Chromatography", *Journal of Chromatographic Science*, vol. 20, Mar. 1982, pp. 97–102.

Mc Guffin, V. L. & Novotny, Milos, "Thermionic Detection in Microcolumn Liquid Chromatography", *Analytical Chemistry*, 1983, 55, pp. 2296–2302.

Patterson, L., "New Uses of Thermionic Ionization Detectors in Gas Chromatography", *Chromatographia*, vol. 16, pp. 107–111.

White, Curt M., Robbat, Albert, Jr. et al, "Evaluation of a Thermionic Ionization Detector for Nitrated Polycyclic Aromatic Hydrocarbons", *Analytical Chemistry*, 1984, 56, pp. 232–236.

Bombick, Daniel, Pinkston, J. David et al, "Potassium Ion Chemical Ionization and Other Uses of an Alkali Thermionic Emitter in Mass Spectrometry", *Analytical Chemistry*, 1984, 56, pp. 396–402.

Fujii, Toshihiro & Arimoto, Hiromi, "Thermionic Ionization Detector with Lanthanum Hexaboride/Silicon Dioxide Thermionic Emitter Material for Gas Chromatography", *Analytical Chemistry*, 1985, 57, 490–493.

Fujii, Toshihiro, Arimoto, Hiromi, "New Sensitive and Selective Detector for Gas Chromatography: Surface Ionization Detector with a Hot Platinum Emitter", *Analytical Chemistry*, 1985, 57, pp. 2625–2628.

Fujii, Toshihiro & Arimoto, Hiromi, "High-Performance Emitters for Use in a Surface Ionization Detector for Gas Chromatography", *Journal of Chromatography*, (1986), 375–382.

Patterson, P., "A Flame Thernionic Ionization Detector for GC", *Chromatographia* 16, p. 102, (1982).

Patterson, P. L., "Recent Advances in Thermionic Ionization Detction for Gas Chromatography", *Journal of Chromatographic Science*, vol. 24, Feb. 1986, pp. 41–52.

Patterson, P. L., "A Comparison of Different Methods of Ionizing CC Effluents", *Journal of Chromatographic Science*, vol. 24, Nov. 1986, pp. 466–472.

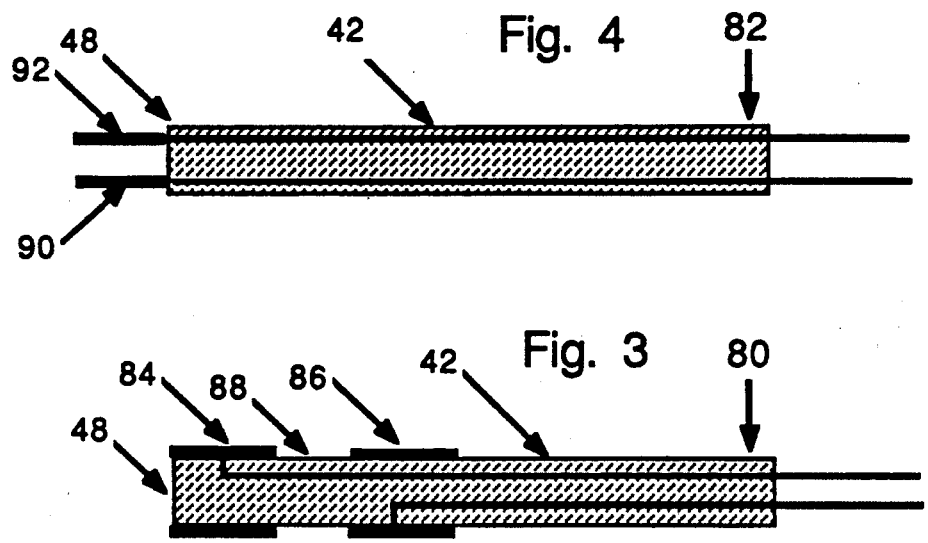
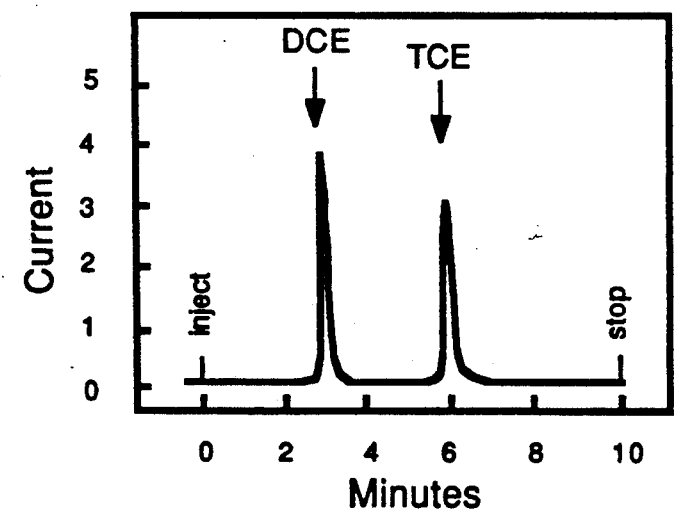
Fig. 5 TID Gas Chromatogram

SYSTEM, DETECTOR AND METHOD FOR TRACE GASES

BACKGROUND OF THE INVENTION

1. Field of the Invention

The present invention relates generally to the detection of small amounts of components in a gaseous mixture. More particularly, it relates to an improved system, detector and detecting method for gas chromatography applications. Most especially, it relates to such an improved system, detector and detecting method for the detection of halogen containing substances.

2. Description of the Prior Art

The art relating to detectors and detecting methods for substances in mixtures is a well-developed one. The following issued patents and other publications give an indication of the scope and content of this prior art.

U.S. Pat. No. 1,421,720, issued July 4, 1920 to C. H. M. Roberts, discloses a detector having two electrodes with an air gap through which a current flows. The magnitude of the current is dependent on the molecular weight of a gas in the gap. The current source in this detector is emitted electrons from a heated, negatively charged electrode. Apparently, temperatures tested with this device were insufficiently high to create selective ionization of halogens. Current is increased by increasing the temperature of the emitting electrode and by increasing the potential gradient across the gap between the electrodes. The presence of chlorine in helium causes a decrease in the emission current of this detector.

U.S. Pat. No. 1,809,115, issued June 9, 1931 to R. H. Goddard, discloses a device for the generation of positive ions using an evaporation source for deposition on a thin platinum cylinder. Volatile metallic substances penetrate the platinum. There is no mention of halogens.

U.S. Pat. No. 2,334,356, issued Nov. 28, 1941 to B. Salzberg et al., discloses an electron emitting vacuum gauge with multiple grids.

U.S. Pat. No. 2,550,498, issued Apr. 24, 1951 to C. W. Rice, discloses a halogen detector based on the generation of positive ions at a heated anode. The presence of an activating material containing alkali metal ions, such as sodium, is needed to produce the positive ions. The activating material is in the form of an impregnated ceramic. A temperature as high as 1200 degrees K. for the anode is required. The electrodes are in the form of filaments, both of which may be heated.

U.S. Pat. No. 2,597,352, issued Dec. 18, 1951 to W. C. White, discloses a detector for trace substances in an atmosphere using intermittent exposure of the detector to the contaminant to avoid variations in response due to excessive depletion of the sensitizer on the anode surface. This disclosure gives a good understanding of the process as developed at that time. U.S. Pat. No. 2,591,485, issued Apr. 26, 1952 to W. C. White, discloses a vacuum leak detector sensitive to halogens, with a slightly different configuration than previous devices.

U.S. Pat. No. 2,795,716, issued June 11, 1957 to J. A. Roberts, discloses an electrical vapor detector similar to that described in the above Rice patent. Detail concerning sensitizing substances for the detection of halogens is given. The temperature range of 700 to 925 degrees C. for the emitter is disclosed. A high alumina content for the core is recommended. The lithium containing metal glass known as b-eucryptite is mentioned. Sensitivity to the four common halogens is demonstrated. This patent emphasizes the composition and configuration of the detector.

U.S. Pat. No. 2,814,018, issued Nov. 19, 1957 to P. D. Zemany, discloses a detector similar to that of the Rice patent, but operated at a reduced pressure, that gives an electron discharge for the detection of halogens. Only the anode is heated.

U.S. Pat. No. 2,897,437, issued July 28, 1959 to W. E. Briggs et al., discloses a system for vacuum leak detection based on the concept of the Rice patent. By keeping signals low, depletion of the sensitizing material on the anode is avoided, resulting in better reproducibility.

U.S. Pat. No. 2,928,042, issued Mar. 8, 1960 to R. B. Lawrence et al., discloses a high vacuum device for the detection of halogens in the form of a leak detector. A heated platinum anode is used.

U.S. Pat. Nos. 3,009,074, issued Nov. 14, 1961; 3,065,411, issued Nov. 20, 1962; 3,071,722, issued Jan. 1, 1963 and 3,144,600, issued Aug. 11, 1964, all to J. A. Roberts, disclose the use of Nichrome V wire electrodes and magnesium silicate ceramics in a simple to manufacture halogen electrical vapor detector, an indicating circuit for a leak detector, additional details for the construction of a practical leak detector, and an electronic circuit to adjust for background and range to give more reproducible and linear response, respectively.

A. Karmen and L. Giuffrida, Nature, 201, 1204 (1964) disclose the enhancement of the response of a hydrogen flame ionization detector to compounds containing halogens and phosphorus. Sodium vapor is introduced from a heated probe. This is probably the first thermionic detector for gas chromatography. A. Karmen, Anal. Chem. 36, 1416 (1964) discloses a specific detector for halogens and phosphorus with two flame detectors in tandem. U.S. Pat. No. 3,372,994, issued Mar. 12, 1968 to L. Guiffrida discloses a modified flame ionization detector with a heated electrode coated with a fused alkali metal salt.

C. H. Hartman, J. Chrom. Sci. 7, 163 (1969), describes an alkali flame detector with a salt tip on the flame input capillary. CsBr is used for detecting phosphorus, and $Rb_2SO_4$ is used for detecting nitrogen B. Kolb and J. Bischoff, J. Chrom. Sci. 12, 625 (1974), disclose a new design of a thermionic nitrogen and phosphorus detector for gas chromatography. They concluded that the mechanism involves gaseous alkali atoms followed by transfer of an electron to a more electronegative gaseous molecule. The emitter electrode is maintained at −130 V. with respect to the collector electrode The emitter electrode is an electrically heated glass bead, containing Rb silicate. B. Kolb, M. Auer and P. Pospisil, J. Chrom. Sci. 15, 53 (1977) disclose a tunable detector selective for carbon, nitrogen and phosphorus. An alkali glass bead source is used. A list of electron affinities is given. B. Kolb, M. Auer and P. Pospisil, J. Chromatography 134, 65 (1977) describe a detector that can be operated as either a flame ionization detector or a thermionic detector. They use a Rb bead heated on a coil and negatively charged. K. Olah, A. Skoze and Zs. Vajta, J. Chrom. Sci. 17, 497 (1979), describe the ionization mechanism of the Kolb device. They assume a cyclic process or reduction of alkali ions at the emitter cathode.

C. A. Burgett, D. H. Smith and H. P. Bente, J. Chromatography 134, 57 (1977), describe a new nitrogen and phosphorus detector and its applications to gas chromatography. The collector is polarized at −240 V., and it is assumed that M+ ions are formed from alkali atoms and recollected on the negatively charged collector cylinder.

P. L. Patterson, J. Chromatography 167, 381 (1978), discloses the selective responses of a flameless thermionic detector. He reports that the emitter gives too high backgrounds when charged positively. A negatively charged emitter is used. P. L. Patterson and R. L. Howe, J. Chrom. Sci. 16, 275 (1978), describe a thermionic nitrogen and phosphorus detector with an alkali-ceramic bead. The voltage applied to the emitter is 0 to −12 V. This is a form of hydrogen flame ionization detector. More positive voltages increase the background current to levels that "mask sample response". U.S. Pat. No. 4,203,726, issued May 3, 1980 to P. L. Patterson, discloses a detector configured like a hydrogen flame ionization detector and having a negatively charged bead emitter that is heated with a resistance wire that also serves as the cathode. The background current increases with temperature according to the Richardson-Dushman equation, i.e., a plot of log (current) against 1/T is a linear function ($e^{-W/T}$), where W is the work function P. L. Patterson et al., J. Chrom. Sci. 20, 97 (1982), describe a thermionic ionization detector with a cylindrical rod thermionic source rather than a bead, used with a low flow of hydrogen (3–6 ml/min.) and an air flow of 150–200 ml/min. A temperature of 400–600 degrees C. in one mode of operation and 600–800 degrees C. in another mode. Negative ions are reported to be formed from electronegative substances. This detector is sensitive to nitrogen, phosphorus and halogens and uses a cesium activator. U.S. Pat. No. 4,524,047, issued June 18, 1985 to P. L. Patterson, discloses a hydrogen flame ionization like thermionic detector with a multiple layered ionization source and a ceramic rod heated internally with the cathode. A temperature range of 100 to 1000 degrees C. is disclosed. The ceramic rod contains an alkali metal compound in primarily alumina. Electric currents originate on the surface of the ceramic coating P. L. Patterson, J. Chrom. Sci. 24, 41 (1986), reviews recent advances in thermionic detection. Four configurations suitable for mounting on a classical hydrogen flame ionization detector are described. In every case, the emitter electrode is also used to provide heat with a heating current flowing through the negatively charged emitter. P. L. Patterson, J. Chrom. Sci. 24, 466 (1986), reviews the common detectors, including photo-ionization detectors, flame ionization detectors, electron-capture detectors and thermionic ionization detectors. The surface temperature of the emitter of the thermionic ionization detector is from 400 to 800 degrees C., and the emitter is maintained negatively to avoid high background currents. He teaches that, "All modern TIDs employ a solid surface composed of a ceramic or glass matrix molded onto an electrical heater wire." He also teaches that, "The ionization produced in the TID is the result of a gas-solid interaction, so there is no indication that equal concentrations of positive and negative ion species are formed, as in the case of the FID and PID." The latter statement is incorrect, since a balance of charges is always required. This demonstrates that TID is still poorly understood.

T. Fujii and H. Arimoto, Anal. Chem. 57, 490 (1985), describe a thermionic detector based on a lanthanum boride bead. They state that their results are consistent with a process of negative surface ionization. T. Fujii and H. Arimoto, Anal. Chem. 57, 2625 (1985), describe a surface ionization detector with a hot platinum, positively charged emitter. They indicate that organic molecules are ionized on the hot metal surface T. Fujii and H. Arimoto, J. Chromatography 355, 375 (1986), found that Ir is a better emitter than Pt in a surface ionization detector. Oxygen improves the surface ionization, and temperatures of 650 degrees C. were used, giving the highest detector response.

While a substantial amount of work has been done with prior art systems, detectors and detecting methods, detector configurations and detecting methods at present do not incorporate optimum conditions for detecting many compounds, for example, organic compounds containing halogens.

SUMMARY OF THE INVENTION

Accordingly, it is an object of this invention to provide an improved system, detector and detection method capable of measuring trace levels of halogen containing substances in a gas stream, such as air, nitrogen or helium.

It is another object of the invention to provide such a system, detector and detection method in which the sensitivity remains constant during a typical measuring interval.

It is a further object of the invention to provide such a system, detector and detection method that will give a constant response during long periods of use at varying levels of exposure to trace halogen gases in a bulk gas stream.

It is still another object of the invention to provide such a system, detector and detection method which is particularly suitable for gas chromatography.

It is a still further object of the invention to provide such a system, detector and detection method which is sensitive to picogram amounts and gives responses which are proportional to sample size.

The attainment of these and related objects may be achieved through use of the novel system, detector and detection method herein disclosed. A detector system in accordance with this invention has a source of a gas stream containing the component to be detected and a detector including a pyrolysis chamber. The first gas stream source is connected to supply the gas stream to the pyrolysis chamber. The detector includes a pair of detector electrodes in the pyrolysis chamber. A heater independent of the pair of detector electrodes is connected to the pyrolysis chamber. A means is connected to the heater for controlling the heater to establish a given temperature in the pyrolysis chamber. A detector circuit is connected to receive an output signal from at least one of the pair of detector electrodes.

A detector in accordance with the invention has a pyrolysis chamber and an input for a gas including a component to be detected to the pyrolysis chamber. There are electrodes in the pyrolysis chamber for ion current generation and collection. A source of an electrical potential is connected to establish a potential difference between the electrodes of between about 5 volts and about 50 volts. A means, such as an ammeter, is connected to the electrodes for measuring electrical current passing between the electrodes. A heater in the form of a tube furnace includes a resistance heater, an insulating layer over the resistance heater, and a thermocouple mounted in the tube furnace. A means for controlling the heater is connected to the heater and to said thermocouple. The means for controlling the heater is configured to establish a predetermined temperature in the pyrolysis chamber.

In the method for detecting a component of a gas stream in accordance with the invention, a pyrolysis chamber for the component in the gas including electrodes substantially free of an alkali metal between which an ion current may flow is provided. A temperature in the pyrolysis chamber between about 700 and 1000 degrees Centigrade is established, and is preferably controlled to within about + or 1 to 2 degrees. Good temperature control is necessary, and desirable, because the sensitivity of the method for detecting halogens increases with temperature in the temperature range of 700 to 1000 degrees Centigrade. Optimum results are obtained with a temperature between about 900 and 1000 degrees Centigrade. The gas containing the component is supplied to the pyrolysis chamber. The resulting ion current between the electrodes is measured.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 3 is a cross-section view of another electrode configuration which can be used in the detector of FIG. 2.

FIG. 4 is a cross-section view of a third electrode configuration which can be used in the detector of FIG. 2.

FIG. 5 is a curve showing results obtained with the system, detector and process of the invention.

DETAILED DESCRIPTION OF THE INVENTION

Figure 1:
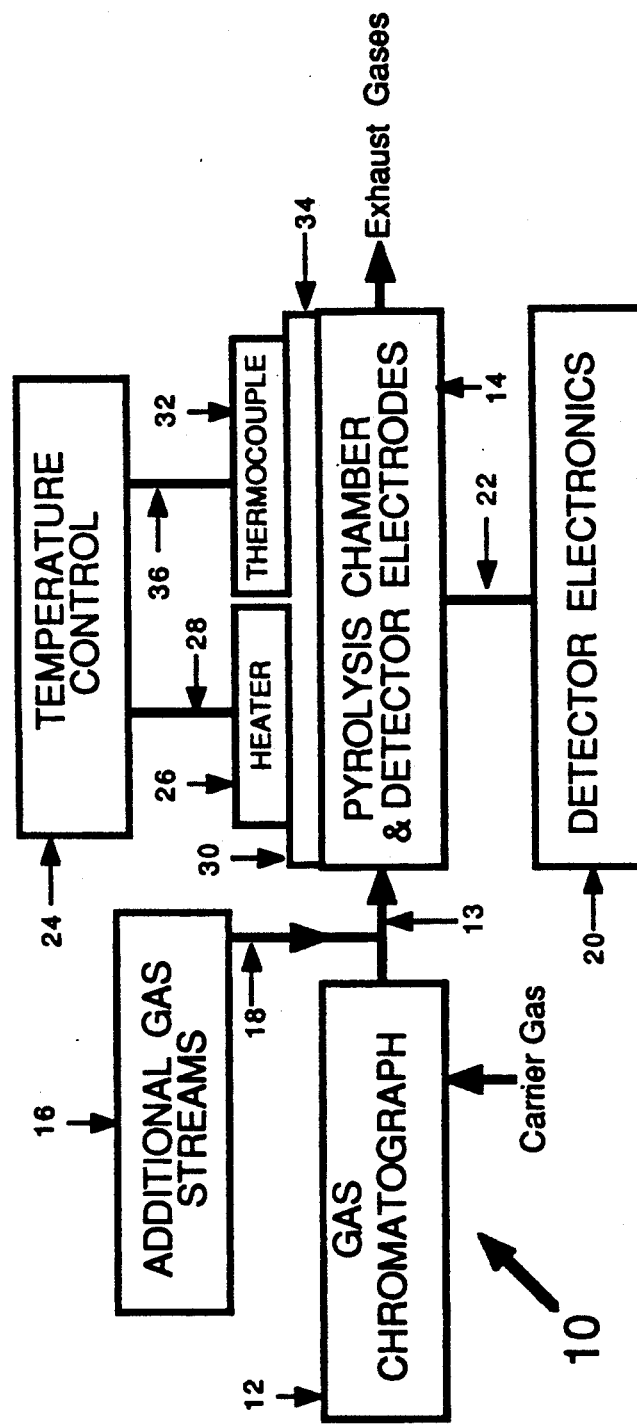
FIG. 1 is a block diagram of a detection system in accordance with the invention.

Turning now to the drawings, more particularly to FIG. 1, there is shown a detector system 10 in accordance with the invention. The system 10 includes a gas chromatograph 12, which is connected by gas line 13 to pyrolysis chamber 14. Sources 16 of additional gas streams are connected by a gas line 18 to the pyrolysis chamber 14. The detector electrodes in the pyrolysis chamber 14 are electrically connected to detector electronics 20 by line 22. A temperature control circuit 24 is electrically connected to heater 26 by line 28. Heater 26 is thermally coupled to the pyrolysis chamber 14 as indicated at 30. The pyrolysis chamber 14 is thermally coupled to thermocouple 32 as indicated at 34. The thermocouple 32 is electrically connected to the temperature control circuit 24 by line 36. The detector electronics 20 is implemented with a Wheatstone bridge circuit calibrated to the component being detected. Alternatively, the detector electronics 20 can be implemented with an analog to digital (A/D) converter and digital circuits providing an equivalent to a Wheatstone bridge. In this form, the detector electronics can be programmable for allowing an easy selection of different components for detection.

Figure 2:
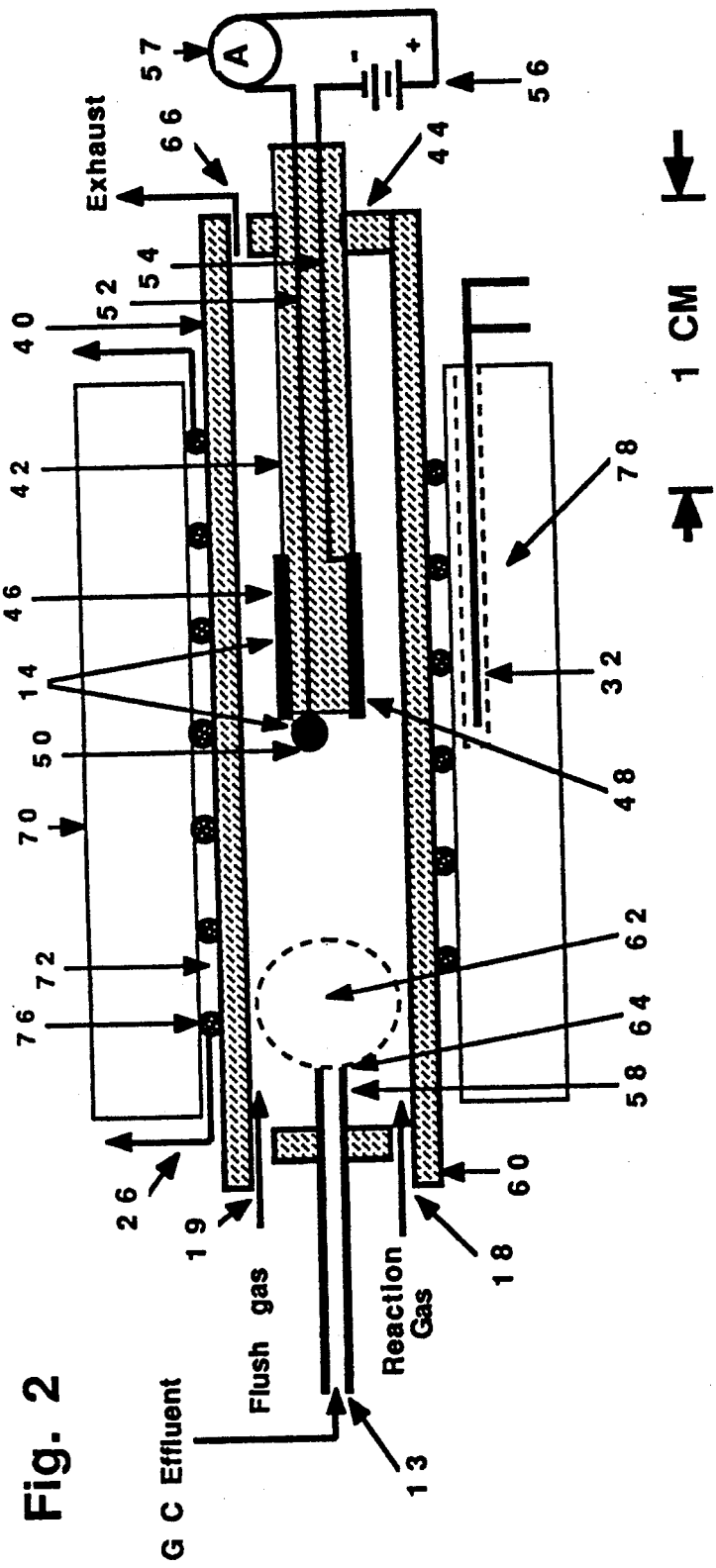
FIG. 2 is a cross-section view of a detector in accordance with the invention.

Details of the pyrolysis chamber and detector electrodes 14, the gas stream inlets 13 and 18, the heater 26 and the thermocouple 32 are shown in FIG. 2. The pyrolysis chamber and electrodes 14 are formed in a generally cylindrical ceramic vessel 40 having an integrally formed electrode support pedestal 42 extending from right end 44 of the vessel 40. A cylindrical platinum, gold, other noble metal or alloy, or other suitable metal cathode 46 is mounted around end 48 of the support pedestal 42. A generally spherical platinum, gold or other suitable metal anode 50 is mounted on the end 48 of the support pedestal 42. No sensitization of the cathode 46 or the anode 50 is required. They are therefore substantially alkali metal free. Connecting wires 52 and 54 embedded in the support pedestal 42 respectively connect an ammeter or other current measuring device 57 to the electrodes 46 and 50 to a potential source 56, which is configured to maintain a potential difference of between about 5 volts and about 50 volts between cathode 46 and anode 50. Polarization of the electrodes may be reversed in the normal mode of operation. The gas chromatography input line 13 terminates in a nozzle 58, integrally formed at left end 60 of the vessel 40. Modifying gas input line 18 connects with the interior of vessel 40 to one side of the nozzle 58. Space 62 between tip 64 of the nozzle 58 and top 48 of the support pedestal 42 forms a thermochemical reaction zone in the vessel 40. Additional gas streams may be introduced at ports 19 and 13. Outlet 66 near the right end 44 of the vessel 40 allows spent reaction product gases to exhaust from the vessel 40.

Heater 26 is in the form of a tube furnace 70 surrounding the vessel 40. The tube furnace 70 has a resistance heating element 72 facing the vessel 40 in the form of a Nichrome or other resistive metal wire 76 and a layer 78 of insulation over the wire 76. The structure of the heater 26 allows precise control of the temperature in the reaction zone, which is critical for obtaining accurate results with the detector In comparison with previously described detectors, where the anode at which the positive ions are formed is also used to provide heat, the result is extreme difficulty in controlling the rate of ion generation. The heater 26 also provides a high enough temperature so that no sensitizing agent is required to produce ions from certain elements, such as halogens. For the detection of halogens, the heater 26 is configured to maintain a controllable temperature of between about 700 degrees and about 1000 degrees Centigrade.

FIGS. 3 and 4 show examples of alternative electrode assemblies 80 and 82, which may be used in place of the electrodes 46 and 50 in the FIG. 2 structure. In FIG. 3, the supporting pedestal 42 has a cylindrical anode 84 mounted around the end 48 of the supporting pedestal 42 and a cylindrical cathode 86 having the same configuration as the anode 84 spaced along side 88 of the supporting pedestal 42 from the anode 84. In FIG. 4, a parallel, rod-like anode 90 and cathode 92 pair extend from the end 48 of supporting pedestal 42. Other than as shown and described, the construction and operation of detectors incorporating the electrode assemblies 80 and 82 is the same as the FIG. 2 detector. In all cases, anodic and cathodic polarizations may be reversed.

The scientific operation of the detector system, detector and method of this invention is as follows 1. The effluent stream 13 (FIG. 2) from the gas chromatograph 12 (FIG. 1) is thermally decomposed in the temperature range of 700 to 1000 degrees Centigrade.

2. An ion current related to the halogen concentration is created in the resulting gas stream between the anode 50 and the cathode 46. The electrodes themselves are either inert or act as catalysts for the ionization, being composed of materials such as platinum or gold. In any event, the electrodes are not consumed in the ionization reaction. The electrodes 46 and 50 may be polarized in the range of 5 or more volts for the configurations of electrodes shown in FIGS. 2-4, since the response of the detector is independent of the applied potential above some minimum value. In practice, voltages of about 5 to about 50 volts have been shown to be operable. It is likely that much higher voltages may be used without increases in signal current, but there is no apparent advantage gained from increasing the voltage above those levels.

The electrodes 46 and 50 must be maintained at a constant temperature because the output signal to the detector electronics increases with temperature. Signals of as much as 6 ions per chlorine atom have been observed at 900 degrees Centigrade. It is apparent that the halogens can participate more than once in the generation of ions.

The ion currents are strongly dependent on the composition of the gases present. The largest currents occur if the gas is predominantly helium. The current decreases by a factor of 3 to 4 if the gas is predominantly nitrogen. It is usually desirable to include some oxygen in the gas, introduced to the reaction zone 62 by the additional gas streams line 18, to avoid buildup of thermal decomposition residues in the reaction zone 62. The effects of oxygen and nitrogen on current levels are similar. The presence of hydrogen, and even water, reduces the ion current markedly.

If the gas stream 13 is free of halogens, there may be an increase in sensitivity due to surface effects. This may result in poor reproducibility, which can be avoided by applying a low and constant level of a halogen containing compound in an additional gas stream added to the gas stream through line 18 ahead of the thermal decomposition reaction zone 62.

In operation, the detector 26 as shown in FIG. 2 produced the gas chromatogram shown in FIG. 5. The detector temperature was 900 degrees Centigrade and the carrier gas was helium. The two peaks represent 0.7 nanograms each of 1,2-dichloroethane (DCE) and trichloroethylene (TCE).

It should now be readily apparent to those skilled in the art that a novel detector system, detector and detection method capable of achieving the stated objects of the invention has been provided. The system, detector and detection method measures trace levels of halogen containing substances in a gas stream, such as air, nitrogen or helium, with a sensitivity that remains constant during the measuring interval The system, detector and detection method gives a constant response during long periods of use at varying levels of exposure to trace halogen gases in a bulk gas stream. The system, detector and detection method is sensitive to picogram amounts and gives responses which are proportional to sample size. These features make the system, detector and detection method particularly suitable for gas chromatography, but it is suitable for a wide variety of other applications as well.

It should further be apparent to those skilled in the art that various changes in form and details of the invention as shown and described may be made. It is intended that such changes be included within the spirit and scope of the claims appended hereto.

What is claimed is:

1. A system for detection of a component in a first gas stream, which comprises a source of the first gas stream containing the component to be detected, a detector including a pyrolysis chamber, said first gas stream source being connected to supply the first gas stream to said pyrolysis chamber, said detector including a pair of detector electrodes in said pyrolysis chamber, the electrodes of said detector comprising an anode and a cathode spaced from said anode and mounted on an insulating support, a source of an electrical potential connected to establish a potential difference between said anode and said cathode, said anode and said cathode being of a conductive material substantially free of an alkali metal, a heater independent of said pair of detector electrodes connected to said pyrolysis chamber, said heater comprises a tube furnace including a resistance heater, an insulating layer over said resistance heater, and a temperature sensor mounted in said tube furnace, means connected to said heater for controlling said heater to establish a given temperature in said pyrolysis chamber, said means for controlling said heater and said heater being configured to establish a temperature between about 700 and about 1000 degrees Centigrade and a detector circuit connected to receive an output signal from at least one of said pair of detector electrodes.

2. The detector system of claim 1 in which said source of the first gas stream comprises a gas chromatograph.

3. The detector system of claim 1 in which the conductive material is platinum, gold or other noble metal or alloy.

4. The detector system of claim 1 in which said source of an electrical potential is configured to establish a potential difference between said anode and said cathode of between about 5 volts and about 50 volts.

5. The detector system of claim 1 in which said detector circuit is configured to measure electrical current passing between said anode and said cathode.

6. The detector system of claim 1 in which said temperature sensor comprises a thermocouple.

7. The detector system of claim 1 in which the insulating support comprises a ceramic.

8. The detector system of claim 1 in which said temperature sensor is mounted adjacent to said detector electrodes.

9. The detector system of claim 1 additionally comprising a source of at least a second gas stream for modifying the first gas stream, said source of at least a second gas stream being connected to supply at least a second gas stream to said pyrolysis chamber.

10. The detector system of claim 9 in which said source of at least a second gas stream includes a source of oxygen.

11. The detector system of claim 9 in which said source of at least a second gas stream includes a source of a halogen.

12. A system for detection of a component in a first gas stream, which comprises a source of the first gas stream containing the component to be detected, a detector including a pyrolysis chamber, said first gas stream source being connected to supply the first gas stream to said pyrolysis chamber, a source of at least a second gas stream for modifying the first gas stream, said at least a second gas source being connected to supply at least a second gas to said pyrolysis chamber, said detector including a pair of detector electrodes in said pyrolysis chamber, a heater independent of said pair of detector electrodes connected to said pyrolysis chamber, means connected to said heater for controlling said heater to establish a given temperature in said pyrolysis chamber, and a detector circuit connected to receive an output signal from at least one of said pair of detector electrodes, the electrodes of said detector comprising an anode and a cathode spaced from said anode and mounted on an insulating support, a source of an electrical potential connected to establish a potential difference between said anode and said cathode, said anode and said cathode being of a conductive material that is substantially alkali metal free, said source of an electrical potential being configured to establish a potential difference between said anode and said cathode of between about 5 volts and about 50 volts, said detector circuit being configured to measure electrical current passing between said anode and said cathode, said means for controlling said heater and said heater being configured to establish a temperature between about 700 and about 1000 degrees Centigrade, said heater comprising a tube furnace including a resistance heater, an insulating layer over said resistance heater, and a temperature sensor mounted in said tube furnace, and said source of at least a second gas stream including a source of oxygen and a source of a halogen.

13. The detector system of claim 12 in which said insulating support comprises a ceramic.

14. The detector system of claim 12 in which said temperature sensor comprises a thermocouple.

15. A gas detector comprising a pyrolysis chamber, an input for a gas including a component to be detected to said pyrolysis chamber, electrodes in said pyrolysis chamber for ion current generation and collection, a source of an electrical potential connected to establish a potential difference between said electrodes, configured to establish a potential difference between said electrodes of between about 5 volts and about 50 volts, means for measuring electrical current passing between said electrodes, a heater comprising a tube furnace including a resistance heater, an insulating layer over said resistance heater, and a temperature sensor mounted in said tube furnace, means for controlling said heater connected to said heater and to said temperature sensor, said means for controlling said heater and said heater being configured to establish a temperature between about 700 and about 1000 degrees Centigrade.

16. The gas detector of claim 15 in which said temperature sensor comprises a thermocouple.

17. The detector of claim 15 further comprising an additional gas inlet for at least one gas to modify the gas stream containing the component to be detected.

18. The detector of claim 15 in which said electrodes are platinum, gold or other noble metal or alloy.

19. The detector of claim 15 in which said electrodes are substantially free of alkali metal salts or oxides.

20. A system for detection of a component in a first gas stream, which comprises a source of the first gas stream containing the component to be detected, a detector including a pyrolysis chamber, said first gas stream source being connected to supply the first gas stream to said pyrolysis chamber, said detector including a pair of detector electrodes in said pyrolysis chamber, a heater free of electrical connection to said pair of detector electrodes connected to said pyrolysis chamber, means connected to said heater for controlling said heater to establish a given temperature in said pyrolysis chamber, a temperature sensor positioned to measure temperature in said pyrolysis chamber and a detector circuit connected to receive an output signal from at least one of said pair of detector electrodes.

21. The detector system of claim 20 in which said heater is outside of said pyrolysis chamber.

22. The detector system of claim 21 in which said heater surrounds said pyrolysis chamber.

23. The detector system of claim 22 in which said temperature sensor is a thermocouple.

* * * * *